United States Patent [19]
Ochs et al.

[11] Patent Number: 6,080,481
[45] Date of Patent: Jun. 27, 2000

[54] HIGHLY FLAVORED DENTAL FLOSS

[75] Inventors: Harold D. Ochs, Flemington; Carol A. Duden, Lambertville; Mark D. Saindon, Princeton; Vipul Davé, Summit, all of N.J.

[73] Assignee: McNeil-PPC, Inc., Skillman, N.J.

[21] Appl. No.: 09/300,965

[22] Filed: Apr. 28, 1999

Related U.S. Application Data

[63] Continuation of application No. 08/970,716, Nov. 14, 1997, abandoned.

[51] Int. Cl.[7] ........................................................ B32B 5/02
[52] U.S. Cl. ........................... 428/372; 428/375; 428/378; 428/394; 132/321; 132/323
[58] Field of Search ..................................... 428/372, 375, 428/378, 393, 394, 158, 159; 132/321, 323; 427/2.29

[56] References Cited

U.S. PATENT DOCUMENTS

| | | |
|---|---|---|
| 3,946,949 | 3/1976 | Ashton et al. .............................. 132/89 |
| 4,033,365 | 7/1977 | Klepak et al. ............................. 132/89 |
| 4,414,990 | 11/1983 | Yost .......................................... 132/89 |
| 5,033,488 | 7/1991 | Curtis et al. ............................ 132/321 |
| 5,209,251 | 5/1993 | Curtis et al. ............................ 132/321 |
| 5,220,932 | 6/1993 | Blass ....................................... 132/321 |
| 5,226,435 | 7/1993 | Suhonen et al. ........................ 132/321 |
| 5,353,820 | 10/1994 | Suhonen et al. ........................ 132/321 |
| 5,357,990 | 10/1994 | Suhonen et al. ........................ 132/321 |
| 5,503,842 | 4/1996 | Fazan et al. ............................. 424/443 |
| 5,819,768 | 10/1998 | Bible et al. ............................. 132/321 |

FOREIGN PATENT DOCUMENTS

| | | |
|---|---|---|
| 423541 | 4/1991 | European Pat. Off. . |
| 764430 | 3/1997 | European Pat. Off. . |
| 2289421 | 11/1995 | United Kingdom . |
| 2317828 | 8/1998 | United Kingdom . |
| WO 9111970 | 8/1991 | WIPO . |

*Primary Examiner*—William Krynski
*Assistant Examiner*—J. M. Gray

[57] ABSTRACT

A highly flavored dental article for cleaning the interproximal surfaces of the teeth such as dental floss comprising one filament having a water-insoluble coating. Flavorant and a flavor enhancer are provided on the outer surface of the coating and within the depth of the coating.

23 Claims, 1 Drawing Sheet

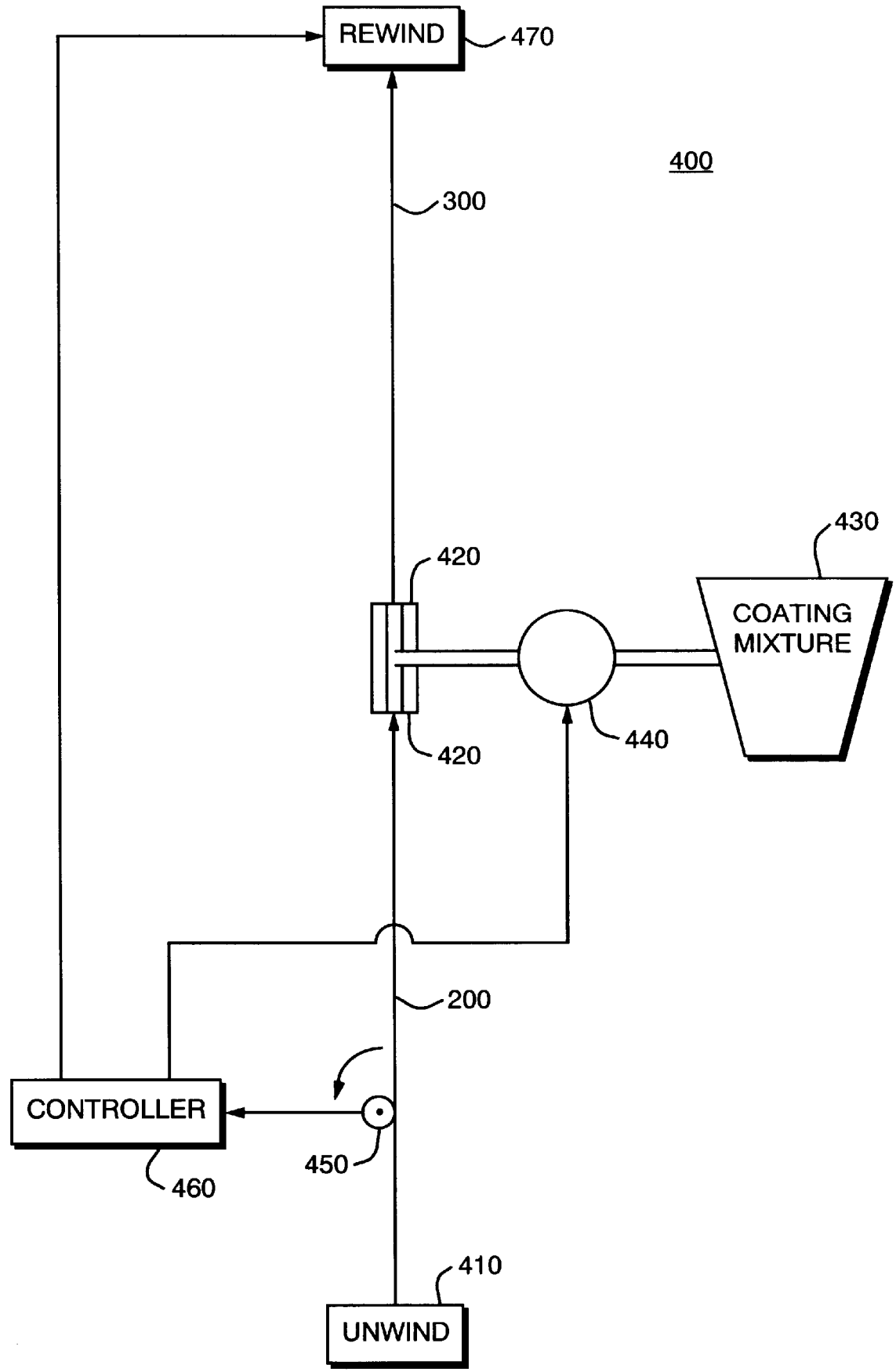

HIGHLY FLAVORED DENTAL FLOSS

This application is a continuation of U.S. patent application No. 08/970,716, filed Nov. 14, 1997, now abandoned.

FIELD OF THE INVENTION

The present invention relates generally to oral hygiene. In particular, the present invention relates to an improved dental article which exhibits a strong, prolonged, high impact flavor. More specifically, the present invention relates to an improved dental floss product which exhibits a strong, prolonged, high impact flavor.

BACKGROUND OF THE INVENTION

The use of flavored dental floss is known in the prior art. Dental flosses are comprised of either several polymeric fibers combined to form a single strand, or alternatively a single polymeric fiber, or monofilament, and are used to remove bacterial debris and plaque from interdental surfaces otherwise unreachable by conventional toothbrushes.

Although the idea of flavoring dental articles is not new, the solution to the problem of providing a strong, high impact flavor on a monofilament floss, and even more particularly PTFE monofilament, has proved perplexing. Concentrated flavor oils are frequently used in prior art dental flosses for flavor. Such flavor oils are volatile at the high temperatures required to melt common carrier materials (e.g. microcrystalline wax, beeswax and the like) used to coat flosses and thus the impact of the flavor is greatly lost during processing.

U.S. Pat. No. 5,165,913 to Hill et al. describes a coating system for floss involving the use of a saliva-soluble surfactant based carrier which is coated onto a multi-filament floss designed to splay upon use, thus releasing the chemotherapeutic agents carried between the fibers. These chemotherapeutic agents may also consist of flavorants and sweeteners used to enhance the flossing experience. Mentioned sweeteners include xylitol, acid saccharin and sodium saccharin.

U.S. Pat. No. 3,943,949 to Ashton et al. describes the use of spray dried flavor particles, in which flavor oils are dispersed in a water-soluble matrix, in order to protect the oil from degradation and volatilization during processing. The water-soluble matrix containing the flavor oils is applied via water-insoluble waxes, preferably microcrystalline wax, to multi-filament flosses. U.S. Pat. No. 4,033,365 to Klepak et al. also uses spray dried flavor particles consisting of flavor oils dispersed in a water-soluble matrix to add flavor to multi-filament flosses. The coating is polymeric and is solubilized in a volatile organic solvent while the spray dried flavor particles are dispersed therein. The floss is passed through a bath containing solvent, binder and flavor and then the volatile solvent is driven off by heat. With the level of flavor and coatings chosen on the Klepak multifilament substrate, the product would be porous exposing a significant amount of the flavor particles for salvation.

Although water-soluble carriers would be expected to provide the best release of flavor upon contact with saliva during flossing, known water-soluble carriers such as polyethylene glycols tend to have low adherence to standard floss materials including nylon 6 and 66. Thus, other formulations have required two separate coating steps, the first of which deposits a water-insoluble wax or polymeric carrier on the floss surface as a "primer" for a second water-soluble coating containing the volatile flavor oil in order to provide a product with desirable characteristics and good flavor.

U.S. Pat. Nos. 5,226,435 and 5,357,990, both to Suhonen et al., disclose the use of a first coat comprising a high melting temperature wax or polymer, preferably microcrystalline wax, which serves to hold the fibers of a multi-filament floss together and retain the desired shape of the floss while a second coating comprising a lower melting temperature material, preferably a blend of polyethylene glycols containing volatile flavor oil is applied. In addition to the flavor oil, the second coating may contain a sweetener, optimally xylitol, to balance the concentrated flavor oil. The lower melting temperature material is thought to prevent the flavor oil from volatilizing during processing as well as to prevent the melting of the inner coating and preserve the shape of the floss.

Similarly, U.S. Pat. No. 4,414,990 to Yost describes the application of a first wax coating to a multi-filament floss article, followed by a second coating of a polymeric material containing fluoride ions. The first coating optionally contains spray dried flavor particles. The second polymeric coating is said to be "capable of hydration whereby the film so formed is water pervious allowing for rapid release of fluoride salt therefrom." See Yost at Col. 3, lines 18–22.

U.S. Pat. No. 5,353,820 to Suhonen et al. describes a floss comprising a multi-filament texturized yarn including an open, porous brush portion with optional threader and/or floss section(s). The article is produced by first applying a polymeric binder coating (preferably nylon) via ethanol solution to the yarn while under tension. Sections of the floss are then exposed to varying degrees of heat, thus driving off varying amounts of solvent, leaving some sections to retract to the original expanded form and the other more heated sections to remain thin and hard. Remaining solvent is then driven off, followed by the application of a second binder coating which contains encapsulated spray dried flavor particles. The second binder should form a water-insoluble coating so as not to dissolve the water-soluble matrix surrounding the flavor particles and should form a hard, flexible polymeric film yet maintain the integrity of the open porous "brush" section of the floss. Polyurethanes soluble in hydrocarbons are preferred. Subsequent applications of the urethane coatings could be made to the optional threader sections to increase the strength of the sections.

Monofilament flosses have become popular among the flossing community due to the reduced amount of fraying and/or shredding associated with them versus multi-filament flosses. In particular, monofilament flosses have been developed using fluorinated polymers such as polytetrafluoroethylene (PTFE) because of the low coefficient of friction (COF) associated with the compounds. The reduced COF allows for easy sliding between tight dental contacts where ordinary multi-filament flosses would perhaps shred or break upon insertion.

Monofilaments, however, are much harder to supply with substantial flavor due to the decreased surface area upon which coating materials can adhere when compared to their multi-filament counterparts. Also, with a monofilament, no splaying of the bundle occurs to expose flavor particles trapped on inner fibers. The surface characteristics of PTFE are not conducive to coating application. U.S. Pat. No. 5,033,488 to Curtis et al. discloses a method for coating expanded, porous PTFE with microcrystalline wax along with oral hygiene actives, coagulating agents, anti-tartar agents and anti caries agents. These additives may also include flavor. The applied coating may also incorporate a water-soluble resin (e.g. polyethylene glycol) in the microcrystalline wax. The coating serves to both increase the COF and to carry the additives.

U.S. Pat. No. 5,503,842 to Fazan et al. mentions in Examples 9–12 a similar coating to U.S. Pat. No. 5,033,488 comprising water-insoluble microcrystalline wax and up to 20% flavorant. The product was deemed to yield "unacceptably low flavorant taste when used." This is due to the fact that the "flavorant in the wax was not solvated so as to provide an acceptable taste." The patent also describes an aqueous emulsion system containing an at least partially water-soluble polymeric binder along with partially water-solubilized medicants and/or flavorants which can be used to coat PTFE or PTFE coated surfaces. The polymeric binder is preferably polyethylene glycol and polyvinyl alcohol. The emulsion is applied to the surface and subsequently dried to remove the water, thus adhering the polymeric binders containing medicants to the PTFE surface. Non-carbohydrate sweeteners such as sodium saccharin and phenylalanine may also be added to the emulsion system.

To improve flavor stability of dental floss, coating formulations have been described whereby spray dried flavors are combined with water-insoluble and water-soluble waxes and coated onto multi-filament yarns. However, no evidence of using flavor enhancers in water-insoluble waxes in coating monofilament yarns, which inherently have a limited surface area, is provided. In order to provide the consumer with a monofilament having a high impact flavor, the coating formulations used must be complex. They typically must contain a water-soluble component and require low process temperatures in order to avoid decomposition of flavor oils. Finally, to provide monofilament dental flosses which deliver sufficient flavor to the consumer, and more specifically for flosses comprising PTFE substrate, the coating compositions used contain significant levels of flavor oils due to the low surface area of the monofilament substrate as compared to a multifilament substrate.

While the above prior art discloses providing flavored dental floss, none of the prior art provides guidance as to a flavored coating composition comprising water-insoluble waxes which provides the consumer with a strong, high impact flavor especially on a monofilament.

It is therefore an object of the present invention to provide a dental article which exhibits a strong, prolonged, high impact flavor.

It is another object of the present invention to provide a dental article having a coating which prevents fraying and/or shredding of the substrate therebelow.

It is a further object of the present invention to provide a dental article that can be easily held (not too slippery) and therefore easily maneuvered between the interproximal spaces of teeth.

It is another further object of the present invention to provide a dental article which can be easily manufactured.

These and other objects and advantages of the invention will become more fully apparent from the description and claims which follow or may be learned by the practice of the invention.

SUMMARY OF THE INVENTION

The present invention is directed to a dental article which exhibits a strong, prolonged, high impact flavor. The dental article comprises a substrate which has a water-insoluble coating coated thereon. The coating has a depth measured from an outside surface of the coating to an exterior surface of the substrate. Flavorant and flavor enhancer are provided both on the outer surface of the coating and within the depth of the coating. The substrate is preferably a monofilament dental floss (such as PTFE) but may also be a dental stimulator, or an interdental cleaning device.

BRIEF DESCRIPTION OF THE DRAWINGS

In order that the manner in which the above-recited and other advantages and objects of the invention are obtained can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

FIG. 1 shows a system for applying a coating to an exterior surface of a dental article substrate, in accordance with a preferred embodiment of the present invention.

DETAILED DESCRIPTION OF THE PREFERRED EMBODIMENT

I. DEFINITIONS

The following definitions are provided to assist in describing the invention.

A. Waxes

The term wax is used as a generic classification of many materials that are either natural or synthetic, and generally these materials are considered waxlike because of their functional characteristics and physical properties. They are solid at ambient temperatures with a relatively low melting point, and capable of softening when heated and hardening when cooled. In general, the higher the molecular weight of a wax, the higher is the melting point.

Waxes are usually classified by their source as natural or synthetic waxes. The waxes obtained from natural sources include animal waxes, such as beeswax; vegetable waxes such as candella and carnauba; mineral waxes and petroleum waxes such as paraffin and microcrystalline wax. The synthetic waxes include Fischer-Tropsch waxes, polyethylene waxes, fatty acid waxes and amide waxes.

Natural Waxes

Petroleum Waxes: These are by far the largest markets of the naturally occurring waxes. Petroleum waxes are further classified into paraffin and microcrystalline waxes.

Paraffin Wax: It is obtained from the distillation of crude oil, and consists mainly of straight-chain saturated hydrocarbons. The molecular weight ranges from 280 to 560 (C20 to C40) and the melting point is about 68° C.

Microcrystalline Wax: It is produced by deoiling the petrolactums or greases obtained by dewaxing deasphalated residual lube stocks or by deoiling the deasphalated tank bottoms that settle out during the storage of crude oil. These waxes are referred to as microcrystalline because the crystals are much smaller than those of paraffin wax. Microcrystalline waxes are composed predominantly of isoparaffinic and naphthenic saturated hydrocarbons along with some n-alkanes. The molecular weight ranges from 450 to 800 (C35 to C60), and produced in two grades with lower (65° C.) and higher (80° C.) melting points.

Animal Waxes: These are usually of insect or mammalian origin.

Beeswax: It is one of the most important commercially available animal waxes and is derived from honeycomb by melting the comb in boiling water and skimming off the crude wax. It is composed of nonglyceride esters of carboxylic and hydroxy acids with some free carboxylic acids, hydrocarbons, and wax alcohols. The melting point of this wax is about 62–65° C. with a flash point of 242° C.

Vegetable Waxes: These are obtained either from leaves and stems or from fruits and seeds. Candelilla and carnauba waxes are the most important commercial vegetable waxes.

Candelilla Wax: It is composed of hydrocarbons (50%), nonglyceride esters, alcohols and free acids. It has a low volume expansion or contraction upon phase change, and melts at about 68–72° C.

Carnauba Wax: It is the hardest and highest melting point of the vegetable waxes. It is composed primarily of nonglyceride esters with small amounts of free acids, resins and hydrocarbons. It melts at about 83–86° C.

Synthetic Waxes:

Fischer-Tropsch Wax: It is a by-product in the synthesis of liquid fuels, such as gasoline and diesel oils, obtained by catalytic hydrogenation of carbon monoxide at high temperature and pressure. It is composed of n-alkanes in the molecular weight range of 600–950 with a melting point of 95–120° C.

Polyethylene Wax: Polyethylenes with molecular weights of 2,000–10,000 have properties of high molecular weight hydrocarbon waxes. These low densities, low molecular weight polyethylenes are made by high-pressure polymerization, low-pressure polymerization with Zieglertype catalysts, or by thermal degradation of high molecular weight polyethylene. They have a melting point of 90–120° C.

Synthetic grades of beeswax, candelilla, and carnauba waxes are also available with similar properties as the natural grades.

Water-Soluble Waxes:

Poly (ethylene glycol): Polymers of ethylene oxide, in the form of relatively low molecular weight liquids and waxes, are commonly referred to as poly(ethylene glycol)—(PEG). Typically, polymers with molecular weight below 20,000 are defined as PEG and those above 20,000 are poly (ethylene oxide)—(PEO). PEGs are available in molecular weights ranging from 1,000 to 20,000, and are all water-soluble. The solubility decreases with increases in molecular weight. The melting point of PEG varies from 45–60° C. depending on molecular weight.

B. Sweeteners and Flavor Enhancers:

Sugar (sucrose) can be used in foods as a bulking agent, preservative, sweetener, and flavor enhancer and as a raw material in the Maillard brewing reaction. Sugars have some disadvantages, the most notable of which is that it can lead to tooth decay. A cavity in a tooth will be formed only if there is bacterial plaque on the surface of a tooth, in the presence of a fermentable carbohydrate, such as sugar. Dental caries involves the growth bacteria on the surface of the tooth, which metabolizes the carbohydrate, forming acid, which then attacks the tooth and can result in decay. Therefore, sweetening agents with low energy value and low cariogenic potential are used which should mimic the properties of sugar. Sweetening agents are divided into two major groups namely bulk sweeteners and intense sweeteners.

Bulk Sweeteners: Bulk Sweeteners include the sugar alcohols, and are generally derived from fruits and vegetables. Sugar alcohols are not easily metabolized by the bacteria in the mouth that cause dental caries. The energy provided by sugar alcohols is less than that of sugar because the sweetener is not fully metabolized by the body. Most commonly used bulk sweeteners are sorbitol, mannitol, xylitol, isomalt, lactitol, maltitol, and hydrogenated starch hydrolysates.

Intense Sweeteners: These are non-nutritive sweeteners as they contribute less than 2% of the energy value in an equivalent unit of sweetening capacity. Furthermore, they are non-cariogenic, i.e. they inhibit the growth of the microorganism associated with dental caries.

Most commonly used intense sweeteners are acesulfarn-K, aspartame, cyclamate, saccharin, thaumatin, sucralose, alitame, neohesperidin dihydrochalcon (DC) and stevioside. All of these intense sweeteners are flavor enhancers. Acesulfam-K continues to taste sweet in the mouth for a longer duration than many other sweetening agents and is therefore used to boost or enhance the sweetness-flavor profile of the product. Aspartame is also able to enhance and prolong the effect of certain flavors in the mouth. It is particularly effective in enhancing acid fruit flavors which means that less flavorant can be incorporated in the formulation. Cyclamate enhances fruit flavors and masks the tartness of some acidic fruits such as grapefruit and lemon. Thaumatin also acts as a flavor enhancer and this function is not affected at high temperatures. Sucralose enhances citrus fruit flavors and the bitter note in chocolate and nuts. Neohesperidin DC is added to chewing gum to increase the rate and duration of flavor release from the gum. This sweetener also enhances fruit and chocolate flavors in food products. Besides bulk sweeteners and intense sweeteners, flavor enhancers may also be selected from menthol derivatives, ginger, ginger-like compounds, low boiling point materials such as ethyl formate and combinations thereof.

C. Encapsulated Flavor Particles:

In order to improve their stability, flavor oils can be dispersed in a suitable matrix by a microencapsulation process. These flavor particles can be made by conventional procedures such as spray-drying emulsions of flavor oils dispersed in a malto-dextrin solution optionally containing a non-toxic gum such as gum arabic. Alternatively, they can be made by extruding, tray-drying or drum-drying the emulsions to form solids which are then ground to the desired particle size. In a still further procedure, the microencapsulated flavor particles can be made by coacervation or aqueous phase separation procedures which yield flavor droplets coated in a non-toxic coating such as gelatin. Suitable flavors include peppermint, spearmint, cinnamon, fruit, and wintergreen. The amount of flavor in the particle can vary from 1 to 30%. Suitable encapsulated flavor particles are described in U.S. Pat. Nos. 3,943,949; 3,957,964; 4,033,365; 4,071,614; 4,386,106; 4,515,769; 4,568,560 and 5,004,595.

D. Surfactants/Emulsifiers:

Emulsification process is the use of surface active agents (emulsifiers) to reduce the surface tension between two phases and therefore allows for the dispersion of one phase (discontinuous phase) into another (continuous) phase to form a stable heterogeneous emulsion. Emulsions are distinguished by their continuous-phase and their discontinuous-phase. Water is the continuous phase in an oil-in-water (O/W) emulsion whereas oil or fat is the continuous phase in a water-in-oil (W/O) emulsion.

The dispersal efficiency of surfactant or emulsifier molecules is a function of the relative interaction of their polar, hydrophilic "heads" with the aqueous phase and of their nonpolar, lipophilic "tails" with the hydrocarbon phase. There is a hydrophile-lipophile balance (HLB) scale that predicts the preference of an emulsifier for oil or water. The higher the HLB value, the more polar (or hydrophilic) the molecule; and the lower the HLB value the more non-polar (hydrophobic) the molecule. On a molecular level, the esters, hydroxyl and carbonyl groups contribute the hydrophilic tendency of the emulsifier, while the hydrocarbon chain of the fatty acid contributes the lipophilic tendency.

The HLB system is a tool for selecting emulsifiers in simple systems, and there is always an element of trial and error. Good results are usually obtained by blending several emulsifiers to achieve a desired HLB value. Knowledge of the HLB number as well as chemical similarity of the substances being blended are needed for successful blending.

Function, source, chemical type, tendency to ionize, and solubility classify emulsifiers. Natural and synthetic emulsifiers are used in formulations. Natural emulsifiers, such as phospholipids, are found in soybeans and eggs. Synthetic emulsifiers may be derived from a polyol and a fatty acid or fat. The polyols most commonly used are glycerin, propylene glycol and sorbitol. Fats and fatty acids are derived from various animal and vegetable sources.

Types of Emulsifiers:

Mono- and Diglycerides: Distilled monoglycerides are emulsifiers containing a minimum of 90% monoglycerides. These are water in oil emulsifiers. These emulsifiers are used to stabilize emulsions, complex with starch and proteins, and affect viscosity. Glyceryl monostearate is distilled monoglyceride produced from fully hydrogenated soybean oil and is composed primarily of stearic acid esters. However, these are starch complexing agents and forms insoluble adducts with amylose.

Propylene glycol monoesters: It is primarily composed of propylene glycol monostearate, and these are water-in-oil emulsifiers due to their lipophilic groups.

Sorbitan Esters and Polysorbate Esters: Sorbitan esters are prepared by reacting sorbitol with common fatty acids (e.g. lauric, palmitic, stearic, and oleic) to form mono or tri esters of sorbitol, sorbitan and sorbide. Polysorbate esters are highly surface active emulsifiers and are made by reacting ethylene oxide with sorbitan esters to increase their hydrophilic properties. These are generally suited for oil-in-water emulsions.

Polyglycerol Esters: These emulsifiers have functional properties similar to those of polysorbates.

Lecithin: It is a naturally occurring mixture of phospholipids commonly found in animal and plant cells. It is a derivative of soybean and consists of phosphatidylcholine (23%), phosphatidylethanolamine (20%), phosphatidylinositol (14%) and phosphatidic acid (8%). The molecular structure of phospholipids contains both a hydrophilic and a hydrophobic moiety, which makes lecithin simultaneously interact with oil and water.

II. Application of the Flavored Coating System to Prepare Dental Floss

The dental floss of the present invention comprises a monofilament substrate with a coating composition comprising a water-insoluble wax, flavor and flavor enhancer and optionally an emulsifier. The coating provides a high impact flavor.

The monofilament dental floss substrate may be formed from polyamides; fluorinated polymers such as polytetrafluoroethylene (PTFE); rayon; polyesters; acetate polymers; polyolefins; block copolymers; cotton; wool; silk; or mixtures thereof. The monofilament may have any desired shaped cross-section. The dental floss of the present invention may be made from a monofilament having a denier of 500–3600, a thickness of 20–250 microns and a tensile strength of no less than 3 lbs. Preferably, the monofilament substrate is made of a fluoropolymer with a geometric cross section, having a denier of 700–2800, a thickness of 25–150 microns and a tensile strength of no less than 3.5 lbs. More preferably, the monofilament substrate is made of porous (expanded) PTFE with a rectangular cross section, having a denier of 900–2000, a thickness of 28–100 microns and a tensile strength of no less than 4 lbs.

The dental floss of the present invention may contain 5–30% by weight (w/w) of coating composition (i.e. weight of coating/weight of substrate plus coating). Preferably, the monofilament dental floss contains coating composition at a level of 5–20% w/w of the coated dental floss and more preferably at a level of 10–15% w/w of the coated dental floss. Further, the coating has a preferably substantially uniform outer surface which lacks openings.

The dental floss of the present invention is typically wound onto a bobbin for convenient dispensing. The dental floss may be maintained in its original orientation or twisted on the bobbin.

The coating composition of the present invention is comprised of water-insoluble wax, flavor, flavor enhancer and may contain an emulsifier to help eliminate phase separation during processing. The water-insoluble wax should have a sufficiently high melting point so that the coating composition will solidify on the floss prior to re-winding the coated floss on the take-up spool. The water-insoluble wax may be natural or synthetic. Preferably, the wax will be selected from petroleum waxes, animal waxes or polyethylene waxes. More preferably, the wax may be beeswax or microcrystalline wax. Suitable waxes may be procured from a variety of sources such as Strahl and Pitch of West Babylon, N.Y. and Witco of Greenwich, Conn.

The flavor component, or flavorant, used should be suitable for use as a dental floss flavor and should contain essential oils that will be compatible with the processing conditions typically used in typical dental floss manufacture. Typically, peppermint, spearmint, cinnamon, fruit and wintergreen natural and artificial flavors, in the form of spray dried, encapsulated flavor particles are used. Suitable flavor particles may be procured from Quest International of Mount Olive, N.J., International Flavor and Fragrances of Dayton, N.J. and Virginia Dare of Brooklyn, N.Y. The amount of flavorant comprises at least about 5% by weight of the water-insoluble coating.

To provide flavor enhancement, bulk sweeteners or intense sweeteners may be used in dental floss coating compositions. Sweeteners may act to prolong the taste of flavor, act to boost the sweetness-flavor profile of a product, mask the tartness of acidic fruit flavors or may increase the rate of flavor release. In order to gain the maximum flavor enhancement on the floss of the present invention, intense sweeteners are preferred. More preferably, saccharin is used because it is non-cariogenic, i.e. it does not promote the growth of the microorganism associated with dental caries. The amount of flavor enhancer comprises at least about $\frac{1}{10}$% by weight of the water-insoluble coating. The flavorant and flavor enhancer are dispersed homogeneously throughout the coating.

Emulsifiers may be used in dental floss coating composition formulations in order to reduce the surface tension between the ingredients thereby allowing for the coating composition to be uniform and remain homogeneous during processing. Emulsifiers may be selected from mono and diglycerides, propylene glycol monoesters, sorbitan esters, polysorbates, polyglycerol esters, lecithin, or combinations thereof, and preferably propylene glycol monoester and/or lecithin. Suitable emulsifiers used in dental floss coating compositions may be EC-25 from Loders Croklaan USA of Glen Ellyn, Ill. and YELKIN SS or YELKIN DS emulsifires from ADM Ross and Rowe Lecithin of Decatur, Ill.

III. Flavor Coating System

Flavored coating systems were prepared by blending waxes, flavors, flavor enhancers, and emulsifiers in a laboratory setting. The mixtures were evaluated for their ability to remain homogeneous both with and without mixing. The following flavored coating systems are illustrated in Table 1.

rin. The spray-dried flavor contains a water-soluble coating of modified starch. When all these ingredients are mixed together (Example 1), complexation occurs between sodium

TABLE 1

Example Coating Systems

| Example | Flavorant | Flavor Enhancer | Carrier | Stabilizer | Comments |
| --- | --- | --- | --- | --- | --- |
| Examples 1–4: Individual Component Compatibility | | | | | |
| Example 1 | 25% Quest 4921 SD "Doublemint" | 1% Sodium saccharin | 74% Beeswax | None | Phase Separation |
| Example 2 | 25% Quest 4921 SD | None | 75% Beesw&x | None | No Phase Separation |
| Example 3 | None | 9.5% Sodium saccharin | 90.5% Beeswax | None | No Phase Separation |
| Example 4 | 6% Quest 4921 | 2% Sodium saccharin | 92% Beeswax | None | No Phase Separation |
| Examples 5–6: Flavor Carrier Compatibility | | | | | |
| Example 5 | 27% Virginia Dare Wintergreen #425 SD | 1% Sodium saccharin | 72% Beeswax | None | No Phase Separation |
| Example 6 | 27% IFF Spicemint SD | 1% Sodium saccharin | 72% Beeswax | None | Phase Separation |
| Examples 7–8: Carrier Wax Compatiability | | | | | |
| Example 7 | 25% IFF Spicemint SD | 2% Sodium saccharin | 73% MCW | None | No Phase Separation |
| Example 8 | 27% Quest 4921 SD | 1% Sodium saccharin | 72% Synthetic Beeswax | None | Phase Separation: Same result as Natural Beeswax |
| Examples 9–14: Stabilizer Evaluation | | | | | |
| Example 9 | 27% Quest 4921 SD | 1% Sodium saccharin | 67% Beeswax | 5% EC-25 | No Phase Separation |
| Example 10 | 25% Quest 4921 SD | 1% Sodium saccharin | 69% Beeswax | 5% Yelkin SS | No Phase Separation |
| Example 11 | 25% Quest 4921 SD | 0.5% Sodium saccharin | 70% Beeswax | 4.5% Glyceryl Monostearate | Phase Separation |
| Example 12 | 25% Quest 4921 SD | 1% Sodium saccharin | 69% Beeswax | 5% DUR-EM 117 | Phase Separation |
| Example 13 | 25% Quest 4921 SD | 1% Sodium saccharin | 69% Beeswax | 5% ICE #2 | Phase Separation |
| Example 14 | 25% Quest 4921 SD | 1% Sodium saccharin | 69% Beeswax | 0.5% Tween 60, 4.5% Span 60 | Phase Separation |

TABLE 2

HLB Values of Emulsifiers Used in Examples 9–14

| Emulsifiers | HLB Value |
| --- | --- |
| Propylene glycol mono and diesters (EC-25) | 2.6 |
| Mono and diglyceride (DUR-EM 117) | 2.8 |
| Monoglyceride (Glyceryl monostearate) | 3.8 |
| Lecithin (YELKIN SS and YELKIN DS) | 4 |
| Sorbitan monostearate (Span 60) | 5 |
| Mono and diglycerides and Polysorbate (ICE #2) | 5.2 |
| Polyoxyethylene (20) sorbitan monostearate (Tween 60) | 14 |

Formulations containing beeswax combined with either spray-dried flavor or flavor enhancer (sodium saccharin, PMC Specialties, Cincinnati, Ohio) are stable (i.e. no phase separation was observed; see Examples 2,3). Additionally, when flavor oils, rather than spray dried flavors, are combined with beeswax and flavor enhancer, the resulting mixtures are stable (Example 4). However, it has been observed that when formulations contain beeswax, spray-dried flavor and flavor enhancer, the coating system is not stable and phase separation occurs (Example 1). The carrier used in Examples 1–4, i.e., beeswax, is composed of nonglyceride esters of carboxylic and hydroxy acids with some free carboxylic acids, hydrocarbons, and wax alcohols. The flavor enhancer used in the formulations is sodium sacchasaccharin, spraydried flavor starch, and beeswax causing it to phase separate.

It is also evident that certain types of starch matrices for the spray drying process are more stable than others, as is evident in Examples 5 and 6. Spray dried flavor particles using similar flavor oils yield different stability results in the beeswax/saccharin combination. It is believed that different starch carrier materials are used by the two suppliers, and these differences affect stability.

The coating formulation is stable when microcrystalline wax (Example 7) is used thus showing that some water-insoluble waxes do not phase separate in fashion displayed by beeswax. Synthetic beeswax is subject to the same phase separation incompatibilities as natural beeswax given otherwise substantially identical formulations (Examples 1,8).

When a certain emulsifier or blend of emulsifiers with an overall HLB value below 4 is added to the coating system in the range of 1.0–10% by weight, the coating system is stable (Examples 9, 10). However, even though the HLB numbers of mono- and diglycerides (DUR-EM 117) and glyceryl monostearate are from 2.8 to 4, the formulation is not stable because of chemical incompatibilities which cause complexation with the particular modified starch coating on the spray-dried flavor particles (Examples 11, 12). Two emulsifiers with HLB values above 4, i.e. ICE #2 and a blend of Tween 60 and Span 60, are shown not to stabilize the coating composition (Examples 13, 14). These results indicate that emulsifiers must be chosen not only by HLB value, but also by compatibility with the other materials of the coating system. Two such emulsifiers that meet both criteria for said coating system (i.e. HLB value below 4 and compatibility with the other materials of the coating system) are lecithin (YELKIN SS (Example 10) and YELKIN DS, both available from Archer Daniels Midland Company, Decatur, Ill.) and propylene glycol esters (EC-25 (Example 9), available from Loders Croklaan, Glen Ellyn, Ill.). Based on the above, the skilled artisan would be able to use suitable alternative emulsifiers determined by routine experimentation.

One preferred coating composition comprises water-insoluble carrier at a level of 48% to 94.9%, flavor component at a level of 5% to 40%, flavor enhancer at a level of 0.1% to 2% and if necessary, in order to achieve coating system stability, a stabilizer at a level of 0 to 10%.

A more preferred coating composition comprises water-insoluble carrier at a level of 48% to 79.9%, spray dried flavor at a level of 20% to 40%, flavor enhancer at a level of 0.1% to 2% and if necessary, in order to achieve coating system stability, a stabilizer at a level of 0 to 10%.

An even more preferred coating composition (Examples 9 and 10) comprises water-insoluble wax (i.e. beeswax) at a level of 64% to 79.5%, spray dried flavor at a level of 20% to 30%, flavor enhancer at a level of 0.5% to 1% and if necessary, in order to achieve coating system stability, a stabilizer at a level of 0 to 5%.

Preferably, the floss of the present invention is made having the constituents shown in Table 3.

TABLE 3

Most Preferred Flavored Coating Composition

| Trade-name | Source | Chemical Description | Weight Percent of component in coating composition |
|---|---|---|---|
| Beeswax | Strahl & Pitsch, West Babylon, NY | Natural Beeswax | 65 |
| Spray Dried Flavor | Quest International, Mount Olive, NJ | Natural and Artificial Flavor in Modified Starch encapsulate | 29 |
| EC-25 | Loders Croklaan, Glen Ellyn, IL | Propylene glycol mono- and diesters of fatty acids, mono- and diglycerides, partially hydrogenated soybean oil with Lecithin, BHT (butylated hydroxy toluene) and citric acid | 5 |
| SYNCAL S Powder | PMC Specialities, Cincinnati, OH | Sodium saccharin | 1 |

The coating process was conducted using the coating apparatus 400 illustrated in FIG. 1 of the drawings. Floss substrate 200 was let off from unwind roll 410 and passed through die station 420 where the coating composition was applied to its exterior surfaces. Die station 420 includes a V-shaped groove (not shown in the drawings) through which floss substrate 200 passes. An opening (not shown in the drawings) is provided at the base of the V-shaped groove for delivering the coating composition in its molten state to the base of the groove. The aforementioned opening in die station 420 is coupled to a heated supply tank 430 by a coating pump 440. Heated supply tank 430 maintains the molten coating composition contained therein at its desired temperature (e.g. 74–100° C., preferably 82–88° C.). The molten coating composition within heated supply tank 430 includes the carrier material, flavorant (e.g. spray dried flavor particles) and flavor enhancer dispersed therein, and the emulsifier if so needed. In a particular embodiment, beeswax (the carrier material) is melted in heated supply tank 430 at 85° C. After an emulsifier is added, mixing is performed for approximately 5 minutes. Saccharin and flavor particles are then added in any desired order. Subsequently, mixing for 30 minutes ensures homogeneity. As the overcoated floss exits die station 420, the molten coating composition cools and solidifies and the finished floss 300 is then rewound onto a take-up roll at rewind station 470.

A velocity sensor 450 is provided for monitoring the velocity of floss 200 passing through coating apparatus 400. The output of velocity sensor 450 is coupled to a controller 460. Controller 460 is also coupled to and provides control signals to pump 440 and to rewind station 470. The control signal provided to pump 440 ensures that, for a given length of floss substrate 200 passing through die station 420, a desired amount of the coating composition is uniformly delivered to die station 420. The control signal provided to rewind station 470 ensures that finished floss 300 is wound onto the take up roll at the same rate that floss substrate 200 is unwound at station 410. Finally, a tensioner (also not shown) is provided for maintaining a tension of about 10–150 grams in the floss as it moves from unwind station 410 to rewind station 470.

Consumer Study

A consumer study was performed comparing mint-flavored floss of the present invention with mint Gore GLIDE. As shown in Table 4, the mint-flavored floss of the present invention was significantly preferred.

| MINT-FLAVORED FLOSS OF PRESENT INVENTION VERSUS MINT GORE GLIDE (n = 48) | | | | |
|---|---|---|---|---|
| | Preferred PRES. INV. | Preferred GORE GLIDE | No Preference | Significance |
| Overall Preference | 28 | 6 | 14 | *** |
| Having the right amount of flavor | 39 | 2 | 7 | *** |
| Having the right type of flavor | 37 | 2 | 9 | *** |
| Sliding easily between teeth (1 no response) | 16 | 12 | 19 | NS |
| Not fraying or shredding during use | 14 | 5 | 29 | NS |
| Not breaking during use (1 no response) | 9 | 2 | 36 | NS |
| Being gentle to the gums | 14 | 6 | 28 | NS |
| Having the right thickness | 13 | 12 | 23 | NS |
| Being easy to grasp the floss to pull from the container/dispenser | 5 | 3 | 40 | NS |
| Breaking off easily/cleanly from the container | 6 | 3 | 39 | NS |
| Being easy to hold while flossing (i.e. not slipping) | 6 | 13 | 29 | NS |
| Not hurting fingers during use | 7 | 7 | 34 | NS |
| Being flexible | 7 | 7 | 34 | NS |
| Having the right amount of waxed coating | 18 | 9 | 21 | NS |
| Having an appealing prior appearance to use | 8 | 7 | 33 | NS |
| Being strong | 5 | 7 | 36 | NS |

-continued

MINT-FLAVORED FLOSS OF PRESENT INVENTION VERSUS MINT GORE GLIDE (n = 48)

| | Preferred PRES. INV. | Preferred GORE GLIDE | No Preference | Significance |
|---|---|---|---|---|
| Cleaning effectively between all teeth | 14 | 4 | 30 | NS |
| Being a floss of high quality | 14 | 8 | 26 | NS |

Significance Levels:
*** = Significant @ p ≦ .01
NS = Not statistically significant (p > .10)

Furthermore, it is to be understood that although the present invention has been described with reference to a preferred embodiment, various modifications, known to those skilled in the art, may be made to the structures and process steps presented herein without departing from the spirit and scope of the invention as set forth in the several claims appended hereto. For example, although the various embodiments described above are directed to several types of dental flosses, other dental articles, such as dental stimulators and inter-dental cleaning devices, may also incorporate the highly flavored coating. Additionally, the spray dried particles comprising the flavorant described above may alternatively be supported on or dispersed in a water-soluble matrix. Further, a supplemental coating may also be applied over the water-insoluble coating. This supplemental coating may be water-soluble and may comprise additional flavorant, flavor enhancer, fluoride, or the like.

What is claimed is:

1. A flavored dental article comprising:
   a monofilament substrate;
   a water-insoluble coating coated on said substrate;
   said coating has a depth measured from an outer surface of said coating to an exterior surface of said substrate; and
   flavorant and flavor enhancer on said outer surface of said coating and within said depth of said coating.

2. The dental article according to claim 1, wherein said monofilament substrate is polymeric.

3. The dental article according to claim 2, wherein said polymeric monofilament substrate is selected from the group consisting of polyamides, fluorinated polymers, rayon, polyesters, acetate polymers, polyolefins, block copolymers, cotton, wool, silk, and mixtures thereof.

4. The dental article according to claim 3, wherein said polymeric monofilament substrate is polytetrafluoroethylene (PTFE) which is a fluorinated polymer.

5. The dental article according to claim 4, wherein said PTFE polymeric monofilament substrate is porous.

6. The dental article according to claim 1, wherein said flavorant compromises spray-dried particles.

7. The dental article according to claim 1, wherein said flavor enhancer is selected from the group consisting of bulk sweeteners, intense sweeteners, menthol derivatives, ginger, ginger-like compounds, ethyl formate and combinations thereof.

8. The dental article according to claim 7, wherein said flavor enhancer is an intense sweetener chosen from the group consisting of acesulfam-K, aspartame, cyclamate, saccharin, thaumatin, sucralose, alitame, neohesperidin dihydrochalcon (DC) and stevioside.

9. The dental article according to claim 8, wherein said intense sweetener is saccharin.

10. The dental article according to claim 7, wherein said flavor enhancer is a bulk sweetener chosen from the group consisting of sorbitol, mannitol, xylitol, isomalt, lactitol, maltitol, and hydrogenated starch hydrolysates.

11. The dental article according to claim 1, wherein said water-insoluble coating is selected from the group consisting of microcrystalline waxes, paraffin waxes, natural beeswax, synthetic beeswax, natural carnauba wax, synthetic carnauba wax, natural candelilla wax, synthetic candelilla wax, ceresine wax, ozokerite wax, polyethylene glycols, polyethylene, Fischer-Tropsch Wax, water-insoluble resins, water-insoluble polymers, and combinations thereof.

12. The dental article according to claim 11, wherein said water-insoluble coating is natural and/or synthetic beeswax.

13. The dental article according to claim 1, wherein the amount of said flavorant comprises at least about 5% by weight of said coating.

14. The dental article according to claim 1, wherein the amount of said flavor enhancer comprises at least about 1/10% by weight of said coating.

15. The dental article according to claim 1, wherein said flavorant and said flavor enhancer are dispersed throughout said coating.

16. The dental article according to claim 1, wherein said coating includes a stabilizing agent.

17. The dental article according to claim 16, wherein said stabilizing agent comprises an emulsifier, surfactant or combination thereof.

18. The dental article according to claim 17, wherein said stabilizing agent is an emulsifier selected from the group consisting of mono and diglycerides, propylene glycol monoesters, sorbitan esters, polysorbates, polyglycerol esters, lecithin, and combinations thereof.

19. The dental article according to claim 18, wherein said stabilizing agent is propylene glycol monoester, lecithin or a combination thereof.

20. The dental article according to claim 1, wherein a water-soluble coating comprising supplemental flavorant is provided on said water-insoluble coating.

21. The dental article according to claim 1, wherein said monofilament substrate is a dental floss.

22. A flavored dental article comprising:
    a monofilament substrate;
    a water-insoluble coating coated on said substrate;
    said coating has a depth measured from an outer surface of said coating to an exterior surface of said substrate; and
    flavorant and flavor enhancer on said outer surface of said coating and within said depth of said coating, wherein said substrate is a dental stimulator.

23. A flavored dental article comprising:
    a monofilament substrate;
    a water-insoluble coating coated on said substrate;
    said coating has a depth measured from an outer surface of said coating to an exterior surface of said substrate; and
    flavorant and flavor enhancer on said outer surface of said coating and within said depth of said coating, wherein said substrate is an interdental cleaning device.

* * * * *